United States Patent [19]
Furutani et al.

[11] Patent Number: 4,731,327
[45] Date of Patent: Mar. 15, 1988

[54] METHOD FOR STABILIZING RECOMBINANT DNA MOLECULES AND ENHANCING THE EXPRESSION THEREOF IN STRAINS OF BACILLUS

[75] Inventors: Yoshio Furutani, Miura; Masaru Honjo; Kazuaki Manabe, both of Yokohama; Hiroaki Shimada, Kamakura; Noboru Tomioka, Mobara, all of Japan

[73] Assignees: Agency of Industrial Science and Technology; Ministry of International Trade and Industry, both of Tokyo, Japan

[21] Appl. No.: 896,583

[22] Filed: Aug. 18, 1986

Related U.S. Application Data

[63] Continuation of Ser. No. 580,123, Feb. 14, 1984, abandoned.

[30] Foreign Application Priority Data

Feb. 19, 1983 [JP] Japan .................................. 58-25523

[51] Int. Cl.$^4$ ........................ C12N 15/00; C12P 21/00
[52] U.S. Cl. .................................. 435/172.3; 935/43; 935/74; 435/68
[58] Field of Search ................ 435/172.3, 68; 935/43, 935/74

[56] References Cited

U.S. PATENT DOCUMENTS

4,495,287  1/1985  Uhlin et al. ........................ 935/43

OTHER PUBLICATIONS

Shivakumar, et al., *Plasmid* 1:405–416 (1978).
Winston, et al., "DNA–Membrane Association is Necessary for Initiation of Chromosomal and Plasmid Replication in *Bacillus subfilis*" *Proc. Natl. Acad Sci* vol. 77(5), pp. 2834–2838, May 1980.
Principles of Gene Manipulation and Introduction to Genetic Engineering, 1980 Blackwell Scientific Publications, pp. 48 through 59.
Construction and Properties of Chimeric Plasmids in *Bacillus subtilis*, Gryczan et al., 1977, pp. 1423 through 1432.
Segregational Instability of pUB110-Derived Recombinant Plasmids in *Bacillus subtilis*, Bron et al., 1985, pp. 235 through 244.
The Third International Conference on Genetics and Biotechnology of Bacilli, 1985, A. T. Ganesan (Stanford), pp. 3, 4, and 51.
Ehrlich, S. D. et al., "DNA Recombination in Plasmids and the Chromosome of *Bacillus subtilis*," A. T. Ganesan & J. A. Hoch (Eds), *Bacillus Molecular Genetics and Biotechnology Applications*, Academic Press, Inc., Orlando, (1986), pp. 27–28.
Hardy, K. G., "Bacillus Cloning Methods", D. M. Glover (Ed.), *DNA Cloning Volume II a Practical Approach*, Irl Press, Oxford, pp. 1–5.

*Primary Examiner*—Thomas G. Wiseman
*Assistant Examiner*—Thomas D. Mays
*Attorney, Agent, or Firm*—Fisher, Christen & Sabol

[57] ABSTRACT

A recombinant DNA molecule, a portion of which includes a vector whose replication is initiated independently of the temperature-sensitive mutant gene of a temperature-sensitive mutant strain of the genus Bacillus as host is introduced into the host. The host is then cultured at a temperature which does not completely inhibit chromosomal DNA replication. By this process, the recombinant DNA molecule can be stabilized in the host and its expression can be enhanced.

17 Claims, No Drawings

METHOD FOR STABILIZING RECOMBINANT DNA MOLECULES AND ENHANCING THE EXPRESSION THEREOF IN STRAINS OF BACILLUS

This application is a continuation of application Ser. No. 580,123, filed Feb. 14, 1984, abandoned.

BACKGROUND OF THE INVENTION

1. Field of the Invention

This invention relates to a method for stabilizing recombinant DNA molecules and enhancing the expression thereof wherein a strain of the genus Bacillus carrying a temperature-sensitive mutation associated with the initiation of chromosomal DNA replication is used as the host.

2. Description of the Prior Art

Conventionally, it is recognized that, when a recombinant DNA molecule is introduced into a bacterium of the genus Bacillus used as the host, the recombinant DNA molecule exhibits very low stability and, therefore, loss or deletion of the inserted foreign DNA fragment may occur during cultivation. In order to prevent such phenomena, it is common practice to use a strain carrying a restriction-deficient mutation or a recombination-deficient mutation (such as recE4 or the like) as the host. However, it has been reported that, even when such a restriction-deficient and recombination-deficient strain is used as the host, the stability of the recombinant DNA molecule is not satisfactorily high and the recombinant DNA itself may undergo recombination during cultivation to take a form different from the original one [Teruo Tanaka, J. Agr. Chem. Soc. Japan, 56, 811, (1982)].

SUMMARY OF THE INVENTION

It is an object of the present invention to provide a method for retaining a recombinant DNA molecule stably within a host.

It is another object of the present invention to provide a method for increasing the copy number of the introduced recombinant DNA molecule and enhancing the expression thereof.

These and other objects of the present invention are accomplished by a method for stabilizing recombinant DNA molecules and enhancing the expression thereof which comprises the steps of providing a temperature-sensitive strain of the genus Bacillus characterized in that the initiation of chromosomal DNA replication is inhibited in a specific temperature range, introducing thereinto a recombinant DNA molecule not requiring the temperature-sensitive mutant gene product for its replication, and culturing the host in a temperature range where the initiation of chromosomal DNA replication of the host is not completely inhibited.

DETAILED DESCRIPTION OF THE PREFERRED EMBODIMENTS

The bacteria of the genus Bacillus which can be used in the practice of the present invention include, for example, *B. subtilis*, *B. amyloliquefaciens*, *B. natto*, *B. cereus*, *B. stearothermophilus* and the like.

Among these useful Bacillus bacteria, the species (such as *B. subtilis*) which have been genetically analyzed to an advanced extent are convenient for use in the practice of the present invention.

In the method of the present invention, there is used a temperature-sensitive mutant strain of the Bacillus species arbitrarily selected which is characterized in that the initiation of chromosomal DNA replication is inhibited in a specific temperature range. Such mutant strains have been relatively closely investigated in *B. subtilis* and specific examples thereof include *B. subtilis* strains dnaA$^{ts}$, dnaB$^{ts}$, dnaC$^{ts}$, dnaE$^{ts}$ and dnaI$^{ts}$. As to the replication of plasmid in these mutant strains, a report has been published by Shivakumar and Dubnau [Plasmid, 1, 405(1978)]. It is recognized in all of these mutant strains that, when they are cultured in a non-permissible temperature range, i.e., at temperatures higher than the upper limit of the temperature range (45° to 48° C.) which permits the initiation of chromosomal DNA replication, the initiation of chromosomal DNA replication is inhibited, but the replication of plasmid is continued to cause an increase in copy number.

The method of the present invention involves the steps of introducing into such a temperature-sensitive mutant strain a recombinant DNA molecule which can replicate without requiring the temperature-sensitive mutant gene product and then cultivating the temperature-sensitive mutant strain used as the host in a temperature range where the initiation of chromosomal DNA replication of the host is not completely inhibited, whereby the introduced recombinant DNA molecule is stably retained within the host. The recombinant DNA molecule to be introduced can be any recombinant DNA molecule that does not require for its replication the product of the temperature-sensitive mutant gene possessed by the host, i.e., any recombinant DNA molecule that can replicate even in a temperature range where the initiation of chromosomal DNA replication of the host is not permitted.

The above-described recombinant DNA molecule may include, as the vector of the DNA molecule, a plasmid whose replication can be initiated independently of the temperature-sensitive mutant gene product, a plasmid fragment including the portion involved in the initiation of its replication, or a complex plasmid whose replication is governed by such a fragment. The plasmid used as the vector of the recombinant DNA molecule can be any plasmid that satisfies the above-described conditions. Specific examples of the above-described plasmid include pSA0501, pE194, pTP5, pUB110 and the like, which are drug-resistant plasmids derived from Staphylococcus bacteria. Specific examples of the above-described complex plasmid include pBD6, pBD8, pBD9 and the like [Gryczan and Dubnau, Proc. Natl. Acad. Sci. USA, 75, 1428(1978)]. However, the preferred plasmid is pUB110 because its structure has been analyzed to the most advanced extent, its cloning site is the only cutting site for available restriction enzymes such as EcoRI, BamHI, BglII, PvuI and AvaI, and its size (4.5 kb) is suitable for use as a vector.

With the temperature-sensitive mutant strains which are associated with the initiation of chromosomal DNA replication and can be used as the host in the method of the present invention, the initiation of chromosomal DNA replication undergoes a higher degree of inhibition as the temperature is increased even in the permissible temperature range for chromosomal DNA replication. On the other hand, the replication of plasmid is continued. Accordingly, the number of recombinant DNA molecules present per cell (i.e., the copy number) can be increased by culturing the host at the highest possible temperature lying in the permissible temperature range for chromosomal DNA replication.

In order to increase the copy number by using any of the above-described temperature-sensitive mutant strains of *B. subtilis*, the host having the recombinant DNA molecule introduced thereinto should be cultured at the highest possible temperature (i.e. 30°–48° C. and preferably 35°–45° C.) lying in the permissible termperature range for chromosonal DNA replication of, for example, 10°–48° C. and preferably 25°–45° C., though the temperature may vary more or less depending on other culture conditions. In this case, not only the recombinant DNA molecule can be stably retained, but also the expression of the recombinant DNA molecule (i.e. the production of the protein coded by the recombinant DNA molecule) can be increased.

In carrying out the method of the present invention, the introduction of the recombinant DNA molecule into the host comprising a temperature-sensitive mutant strain associated with the initiation of chromosomal DNA replication can be accomplished according to any of the commonly used methods. Examples of these introduction methods include the protoplast transformation method [Chang, Molec. Gen. Genet., 168, 111 (1979)] and the competent cell method [Content and Dubnau, Molec. Gen. Genet., 167, 251 (1979)]. It is to be understood, however, that the present invention is not limited thereto and any other method may be employed for this purpose.

As described above, the method of the present invention makes it possible to retain a recombinant DNA molecule stably within a host and increase the copy number of the recombinant gene as required, for example, in order to increase the production of the protein coded by the recombinant gene. More specifically, where a recombinant DNA molecule comprises a plasmid having inserted thereinto a gene coding a specific enzyme protein, the method of the present invention permits the recombinant DNA molecule to be stably retained within a *B. subtilis* host. Accordingly, even when the host of the recombinant DNA molecule is cultured on an industrial scale for a long period of time in order to produce the enzyme protein, the inserted gene coding the enzyme protein are not deleted from the plasmid but stably retained. Moreover, by selecting a suitable culture temperature, the copy number of the recombinant DNA molecule and hence the expression thereof can be increased to result in an increased production of the enzyme.

The present invention is further illustrated by the following examples:

EXAMPLE 1

The chromosomal DNA of *B. amyloliquefaciens* strain F was digested with the restriction enzyme EcoRI and the resulting fragments of various sizes were ligated with the plasmid pUB110 cut with the restriction enzyme EcoRI. Thus, there was obtained a mixture of recombinant DNA molecules comprising chromosomal DNA fragments of various sizes inserted into pUB110. After this recombinant DNA molecule mixture was introduced into *B. subtilis* according to the protoplast transformation method, a *B. subtilis* transformant strain FERM-BP186 (a stock strain maintained in the Fermentation Research Institute Agency of Industrial Science and Technology, 1-3, Higashi 1 chome Yatabe-machi Tsukuba-gun Ibaraki-ken 305, Japan) having markedly increased protease activity was selected. A recombinant DNA molecule was prepared from this transformant strain and named pNP718. When this pNP718 was digested with EcoRI and analyzed by electrophoresis through a 1.0% agarose gel, it was found that a ca. 4.0 kb chromosomal DNA fragment of *B. amyloliquefaciens* strain F was inserted in the plasmid pUB110.

Using the competent cell method, the recombinant DNA molecule pNP718 thus obtained was introduced into various strains of *Bacillus subtilis* including the temperature-sensitive mutant strain 1A20 (dnaC30$^{ts}$) associated with the initiation of chromosomal DNA replication (a stock strain maintained in the Bacillus Genetic Stock Center, the Ohio State University, Columbus, Ohio, U.S.A.), the recombination-deficient strain 1A'46 (a stock strain maintained in the same Center) and the restriction-deficient strain 1A253 (a stock strain maintained in the same Center). The resulting transformants having increased protease productivity were implanted on a casein-agar culture medium containing kanamycin (20 μg/ml) and incubated at 37° C. for 24 hours. Thereafter, the procedure comprising implantation on the kanamycin (20 μg/ml)-containing casein-agar culture medium and incubation at 37° C. was repeated every day. Thus, the stability of pNP718 was evaluated by using protease productivity as an index. Protease productivity was tested by inoculating a casein-kanamycin-agar culture medium with 100 colonies of each transformant and examining the size (diameter) of the halo formed around each colony. When the size of a halo was 2.0 times greater than that observed in the control strain (i.e., the corresponding mutant strain into which pUB110 had been introduced), the halo was considered to be a large halo and the percentages of large haloes among all haloes was calculated.

The results thus obtained are shown in Table 1. As is evident from Table 1, *B. subtilis* strain 1A20 (dnaC30$^{ts}$) carrying a temperature-sensitive mutation associated with the initiation of chromosomal DNA replication continued to form a large halo stably for 30 days. In contrast, the control strains lacking the temperature-sensitive mutation for the initiation of chromosomal DNA replication showed a tendency for the percentage formation of large halos to decrease over a period of days. The same tendency was also noted in the restriction-deficient and recombination-deficient mutant strain.

In all strains, the capacity for colony formation serving as an index to their growth on the kanamycin-containing casein-agar culture medium remained normal for 30 days, without regard to the size of the halo.

Then, using the method of Gryczan et al. [Gryczan et al., J. Bacteriol., 134, 318(1978)], a plasmid was prepared from the transformed strain 1A20 which had been cultured for 30 days. When this plasmid was digested with various restriction enzymes and analyzed, it was found to be identical with the initially introduced recombinant DNA molecule pNP718 and to remain unchanged. On the other hand, plasmids were similarly prepared from the transformed strains 1A46, 1A253 and 1A253-E4 which ceased to form a large halo after being cultured for 30 days, but exhibited normal colony formation on the kanamycin-containing casein-agar culture medium. When the plasmids isolated from these strains were digested with various restriction and analyzed, it was found that the 4.0 kb DNA fragment derived from the chromosomal DNA of *B. amyloliquefaciens* strain F had been deleted from all of them. Moreover, it was confirmed from the cutting patterns of the restriction enzymes that these plasmids were identical with pUB110.

It can be seen from these results that, in the temperature-sensitive mutant strain 1A20 associated with the initiation of chromosomal DNA replication, the recombinant DNA molecule pNP718 is very stably retained even when compared with the restriction-deficient and recombination-deficient strain 1A253-E4 and the DNA fragment derived from chromosomal DNA is not deleted even after being cultured for a long period of time.

TABLE 1

| Type of Experiment | B. subtilis strain | | | Percentage of large haloes | | |
|---|---|---|---|---|---|---|
| | Stock Center No.* | Original code | Genetic character | After 10 days | After 20 days | After 30 days |
| Method of the invention | 1A20 | 1A20 | $dnaC30^{ts}$ (temperature sensitivity for the initiation of the replication of chromosomal DNA) | 100 | 100 | 100 |
| Control | 1A46 | BD224 | recE4 (lack of recombination) | 82 | 25 | — |
| | 1A253 | RM125 | $r_M^- m_M^-$ (lack of restriction) | 45 | 18 | — |
| | | 1A253-E4** | $r_M^- m_M^-$ recE4 (lack of restriction and recombination) | 88 | 75 | 47 |

[Notes]
*The registration number at the Bacillus Genetic Stock Center, the Ohio State University.
**A strain prepared by transforming the parental strain 1A253 with a chromosomal DNA fragment of the strain 1A46.

EXAMPLE 2

Using the competent cell method, the recombinant DNA molecule pNP718 prepared in Example 1 was introduced into B. subtilis strains 1A20 (dnaC30$^{ts}$), 1A46 (recE4) and 1A253 ($r_M^- m_M^-$) (all of which are stock strains maintained in the Bacillus Genetic Stock Center, the Ohio State University) to obtain transformants having increased protease productivity. The BY culture medium (containing 0.5% meat extract, 1% polypeptone, 0.2% yeast extract and 0.2% NaCl and adjusted to pH 7.2) was inoculated with each of these transformants and incubated at 37° C. or 30° C. for 18 hours. Then, the protease activity of the supernatant of the culture medium was determined according to the casein digestion method [Jikken Nogei Kagaku, p. 284, Asakura Shuppan (1978)]. The results thus obtained are shown in Table 2.

It can be seen from these results that, when the temperature-sensitive mutant strain 1A20 associated with the initiation of chromosomal DNA replication was used as a host and cultured at 37° C., a greater amount of protease was secreted than in the cases where the strains lacking the temperature-sensitive mutation were used as hosts and cultured at 37° C.

TABLE 2

| Type of Experiment | Host strain | Genetic character | Relative protease activity | |
|---|---|---|---|---|
| | | | 30° C. | 37° C. |
| Method of the invention | 1A20 | $dnaC30^{ts}$ | 103 | 181 |
| Control | 1A46 | recE4 | 92 | 129 |
| | 1A253 | $r_M^- m_M^-$ | 105 | 132 |
| | B. amyloliquefaciens strain F | | 100 | 106 |

[Notes]
*The relative protease activity was expressed as a percentage of the protease activity obtained by culturing B. amyloliquefaciens at 30° C. for 18 hours.

EXAMPLE 3

Chromosomal DNA was prepared from B. subtilis strain 1A20 (dnaC30$^{ts}$) in the usual manner. Using this DNA, the restriction-deficient mutant strain 1 A253 ($r_M^- m_M^-$) was transformed to obtain a transformant strain (1A253dnaC) having temperature sensitivity associated with the initiation of chromosomal DNA replication. The recombinant DNA molecule pNP718 prepared in Example 1 was introduced into the strains 1A253dnaC and 1A253, and transformant strains having increased protease productivity were selected. Then, plasmids were prepared from these transformant strains according to the method of Gryczan et al. When these plasmids were digested with the restriction enzyme EcoRI and subjected to electrophoresis through a 1.0% agarose gel, the inserted chromosomal DNA fragment of each plasmid was found to have the same size (4.0 kb) as pNP718. Thereafter, in the same manner as described in Example 1, the strains 1A253dnaC and 1A253 having pNP718 introduced thereinto were implanted on a casein-agar culture medium containing kanamycin (20 μg/ml) and the stability of pNP718 was evaluated by using the ability to form a large halo as an index. As a result, it was found that, in the strain 1A253dnaC carrying a temperature-sensitive mutation associated with the initiation of chromosomal DNA replication, the percentage of large haloes was 100% even after a period of 20 days. In the strain 1A253, however, the percentage of large haloes decreased to 47% after 10 days. When a plasmid was prepared from the strain 1A253dnaC having continued to form a large halo stably for 20 days, digested with various restriction enzymes and analyzed by electrophoresis through a 0.7% agarose gel, this plasmid was found to be identical with pNP718.

It can be seen from the above-described results that the recombinant DNA molecule can also be stably retained, without being deleted, in the strain 1A253dnaC carrying the temperature-sensitive mutation associated with the initiation of chromosomal DNA replication which has been introduced by transforming the restriction-deficient strain 1A253 with the chromosomal DNA of the strain 1A20.

EXAMPLE 4

The recombinant DNA molecule pNP718 was introduced into each of the strains 1A253dnaC and 1A253 (described in Example 3), 1A20 and 1A253-E4 (described in Example 1) and transformant strains having increased protease productivity were selected.

The TBAB agar culture medium (Difco) containing kanamycin (20 μg/ml) was inoculated with 100 colonies of each transformed strain, incubated at 37° C. for 18 days and then allowed to stand at room temperature for 18 days. After 18 days, each colony of each strain was implanted on a casein-agar culture medium containing kanamycin (20 μg/ml), incubated at 37° C. for 18 hours and then examined for the percentage of large haloes. The results thus obtained are shown in Table 3.

It can be seen from these results that, in the temperature-sensitive mutant strains 1A20 and 1A253 associated with the initiation of chromosomal DNA replication, all of the 100 colonies had the ability to form a large halo even after a period of 18 days. When plasmids were prepared from both strains and analyzed, these plasmids were found to be identical with pNP718.

TABLE 3

| Strain | Genetic character | Percentage of large haloes |
|---|---|---|
| 1A253 | $r_M^- m_M^-$ | 19 |
| 1A253dnaC | $r_M^- m_M^- dnaC30^{ts}$ | 100 |
| 1A20 | $dnaC30^{ts}$ | 100 |
| 1A253-E4 | $r_M^- m_M^- recE4$ | 72 |

EXAMPLE 5

Using Chang's protoplast transformation method, the recombinant DNA molecule pNP718 prepared in Example 1 was introduced into each of B. subtilis strains 1A18(dnaA13$^{ts}$), 1A19(dnaB19$^{ts}$), 1A22(dnaE20$^{ts}$), 1A26(dnaI102$^{ts}$) and 1A253($r_M^- m_M^-$) (all of which are stock strains maintained in the Bacillus Genetic Stock Center, the Ohio State University). Thus, there were obtained transformant strains having increased protease productivity. The TBAB culture medium (Difco) containing kanamycin (20 μg/ml) was inoculated with 100 colonies of each transformant strain and incubated at 37° C. for 24 hours. This procedure was repeated every day. After 10, 20 and 30 days, the stability of pNP718 was evaluated in the same manner as described in Example 1, using protease activity as an index.

The results thus obtained are shown in Table 4. As is evident from Table 4, the strains carrying a temperature-sensitive mutation associated with the initiation of chromosomal DNA replication continued to form a large halo stably for 30 days, whereas 49% of the 1A253 strain used as a control lost the ability to form a large halo in 10 days.

In all strains, the capacity for colony formation serving as an index to their growth on the kanamycin-containing TBAB culture medium was found to remain normal for 30 days, without regard to the size of the halo. Then, using the method of Gryczan et al. as in Example 1, a plasmid was prepared from the large halo-forming transformants of each dna$^{ts}$ mutant strain after being cultured for 30 days. Upon analysis, these plasmids were found to be identical with the initially introduced recombinant DNA molecule pNP718 and remain unchanged. On the other hand, a plasmid was similarly prepared from the transformants of the strain 1A253 which had lost the ability to form a large halo after being cultured for 30 days, but could normally grow on the kanamycin-containing TBAB culture medium. Upon analysis of this plasmid, it was found that the inserted 4.0 kb DNA fragment derived from the chromosomal DNA of B. amyloliquefaciens strain F had been deleted from pNP718. Moreover, it was confirmed from the cutting patterns of restriction enzymes that this plasmid was identical with pUB110.

TABLE 4

| Type of Experiment | B. subtilis strain Stock Center No.* | B. subtilis strain Genetic character | Percentage of large haloes After 10 days | Percentage of large haloes After 20 days | Percentage of large haloes After 30 days |
|---|---|---|---|---|---|
| Method of the invention | 1A18 | dnaA13$^{ts}$ | 100 | 100 | 98 |
|  | 1A19 | dnaB19$^{ts}$ | 100 | 97 | 97 |
|  | 1A22 | dnaE20$^{ts}$ | 100 | 95 | 90 |
|  | 1A26 | dnaI102$^{ts}$ | 100 | 100 | 94 |
| Control | 1A253 | $r_M^- m_M^-$ | 51 | 24 | — |

[Notes]
*The registration number at the Bacillus Genetic Stock Center, the Ohio State University.

What is claimed is:

1. A method for stabilizing and enhancing expression of recombinant DNA molecules comprising
   (a) providing a temperature-sensitive mutant strain of genus Bacillus in which an initiation of chromosomal DNA replication is inhibited in a specific temperature range,
   (b) introducing a recombinant DNA molecule into the temperature-sensitive mutant strain having a vector with a replication origin of pUB110 in which replication is initiated independently of a temperature-sensitive mutant gene of the temperature-sensitive mutant strain and
   (c) culturing the temperature-sensitive mutant strain in a temperature range from and including 30° C. to below 45° C. and where initiation of chromosomal DNA replication of the temperature-sensitive mutant strain is partially inhibited,
such that said recombinant DNA molecules during said chromosomal DNA replication are stably retained and a copy number of said recombinant DNA molecules is increased.

2. A method as claimed in claim 1 wherein the temperature-sensitive mutant strain is a temperature-sensitive mutant strain of Bacillus subtilis.

3. A method as claimed in claim 1 wherein the temperature-sensitive mutant strain, having a temperature-sensitive mutation located in a gene involved in initiation of chromasomal DNA replication, is a member selected from the group consisting of Bacillus subtilis strains dnaA$^{ts}$, dnaB$^{ts}$, dnaC$^{ts}$, dnaE$^{ts}$, and dnaI$^{ts}$.

4. A method as claimed in claim 2 wherein the temperature-sensitive mutant strain is a member selected from the group consisting of Bacillus subtilis strains dnaA$^{ts}$, dnaB$^{ts}$, dnaC$^{ts}$, dnaE$^{ts}$, and dnaI$^{ts}$.

5. A method as claimed in claim 1 wherein the temperature-sensitive mutant strain, into which the recombinant DNA molecule is introduced, is cultured at the highest temperature at which
(i) the growth of the temperature-sensitive mutant strain is possible; and
(ii) the initiation of chromosomal DNA replication of the temperature-sensitive mutant strain is partially inhibited.

6. A method as claimed in claim 2 wherein the temperature-sensitive mutant strain, into which the recombinant DNA molecule is introduced, is cultured at the highest temperature which
(i) the growth of the temperature-sensitive mutant strain is possible; and
(ii) the initiation of chromosomal DNA replication of the temperature-sensitive mutant strain is partially inhibited.

7. A method as claimed in claim 3 wherein the temperature-sensitive mutant strain, into which the recombinant DNA molecule is introduced, is cultured at the highest temperature at which
(i) the growth of the temperature-sensitive mutant strain is possible; and
(ii) the initiation of chromosmal DNA replication of the temperature-sensitive mutant strian is partially inhibited.

8. A method as claimed in claim 4 wherein the temperature-sensitive mutant strain, into which the recombinant DNA molecule is introduced, is cultured at the highest temperature at which
(i) the growth of the temperature-sensitive mutant strain is possible; and
(ii) the initiation of chromosomal DNA replication of the temperature-sensitive mutant strain is partially inhibited.

9. A method as claimed in claim 3 wherein the temperature-sensitive mutant strain, into which the recombinant DNA molecule is introduced, is cultured at a temperature ranging from 35° C. to below 45° C.

10. A method as claimed in claim 4 wherein the temperature-sensitive mutant strain, into which the recombinant DNA molecule is introduced, is cultured at a temperature ranging from 35° C. to below 45° C.

11. A method as claimed in claim 9 wherein the temperature-sensitive mutant strain, into which the recombinant DNA molecule is introduced, is cultured at a temperature ranging from about 37° C. to below 45° C.

12. A method as claimed in claim 10 wherein the temperature-sensitive mutant strain, into which the recombinant DNA molecule is introduced, is cultured at a temperature ranging from about 37° C. to below 45° C.

13. A method as claimed in claim 1 wherein said recombinant DNA molecules during said chromosomal replication are stably retained, as when cultivation includes transplanting the temperature-sensitive mutant strain culture to correspondingly fresh culture medium every 24 hours, for at least 10 days.

14. A method as claimed in claim 13 wherein said recombinant DNA molecules during said chromosomal replication are stably retained for at least 18 days.

15. A method as claimed in claim 14 wherein said recombinant DNA molecules during said chromosomal replication are stably retained for at least 20 days.

16. A method as claimed in claim 15 wherein said recombinant DNA molecules during said chromosomal replication are stably retained for at least 30 days.

17. A method as claimed in claim 3 wherein the temperature-sensitive mutant strain, into which the recombinant DNA molecule is introduced, is cultured at a temperature of about 37° C.

* * * * *